United States Patent [19]

Miller et al.

[11] Patent Number: 4,874,733

[45] Date of Patent: Oct. 17, 1989

[54] COBALT FISCHER-TROPSCH CATALYSTS HAVING IMPROVED SELECTIVITY

[75] Inventors: James G. Miller, Pearl River; Jule A. Rabo, Armonk, both of N.Y.

[73] Assignee: UOP, Des Plaines, Ill.

[21] Appl. No.: 72,748

[22] Filed: Jul. 13, 1987

[51] Int. Cl.$^4$ .............................................. B01J 29/14
[52] U.S. Cl. .......................................... 502/74; 502/66
[58] Field of Search ..................... 502/66, 74; 518/715

[56] References Cited

U.S. PATENT DOCUMENTS

| | | | |
|---|---|---|---|
| 4,293,446 | 10/1981 | Butter et al. | 502/66 |
| 4,617,283 | 10/1986 | Coughlin | 502/66 |
| 4,652,538 | 3/1987 | Rabo et al. | 502/66 |
| 4,665,042 | 5/1987 | Budge | 502/66 |
| 4,672,048 | 6/1987 | Ward | 502/66 |

FOREIGN PATENT DOCUMENTS 150102 9/1962 U.S.S.R. .

OTHER PUBLICATIONS

Anderson, Robert B., The Fisher-Tropsch Synthesis, Academic Press, Orlando, Florida, 1984, pp. 123-129.
Dent, A. L., and Lin, M., Adv. Chem. Ser., 178, pp. 47-63.
Eidus, Ya. T. et al., Scientific Selection of Catalysts, Daniel Davey & Company, Jerusalem, 1968, pp. 206-213.

Primary Examiner—Carl F. Dees
Attorney, Agent, or Firm—Thomas K. McBride

[57] ABSTRACT

A cobalt Fischer-Tropsch catalyst having an improved steam treated, acid extracted LZ-210 support is taught. The new catalyst system demonstrates improved product selectivity at Fischer-Tropsch reaction conditions evidenced by lower methane production, higher $C_5+$ yield and increased olefin production.

3 Claims, No Drawings

COBALT FISCHER-TROPSCH CATALYSTS HAVING IMPROVED SELECTIVITY

STATEMENT

The Government of the United States of America has rights to this invention pursuant to Contract No. DE-AC22-84PC70028 awarded by the U.S. Department of Energy.

FIELD OF THE INVENTION

The present application relates to the field of cobalt Fischer Tropsch catalysts in combination with an improved molecular sieve support.

BACKGROUND OF THE INVENTION

Iron Fischer-Tropsch (F-T) catalysts have generally been preferred commercially over cobalt based catalysts and are presently the only commercial F-T catalyst used.

In the conversion of synas ($CO+H_2$ mixture) in the Fischer-Tropsch reaction cobalt catalysts have the benefit of higher activity and better selectivity to motor fuels, they suffer from their inherent production of excess methane (an undesirable product) as well as the paraffinic nature of the product. It would be an important catalyst improvement if a stable cobalt F-T catalyst was discovered which demonstrated reduced methane production, increased C5+ yield and improved olefin content, especially in the C5 range.

There is a reasonable amount of prior art dealing with Fischer-Tropsch metals combined with molecular sieve components. The most recent prior art pertinent to this invention is a patent issued to J. A. Rabo et al., U.S. Pat. No. 4,652,538, and the prior ar cited within.

An excellent review of past publications on cobalt Fischer-Tropsch catalyst was reported by R. B. Anderson, "The Fischer Tropsch Synthesis", Academic Press, Orlando Fla, 1984. In the review are lists of promoters and catalysts studied in the past, included are sightings of the use of Mn and Zr promoters. Listed below is a summary of the information presented in this article related to the use of the Mn and Zr promoters. Fischer and Koch showed Mn added to a cobalt kieselguhr catalyst was effective at shifting the product distribution toward heavier product as was also observed for the catalysts in this invention. Work by Eidus and Bulanova showed a similar effect on the addition of $ZrO_2$ to the same type of catalyst, this was not observed upon our addition of $ZrO_2$ to the Mn promoted Co/TC-123 catalyst system. No work to our knowledge has been reported on the use of a combined Mn and Zr promoted catalyst.

Dent, A. L. and Lin, M., Adv. Chem. Ser. 178,47 (1979) reported that the addition of Mn to a cobalt alumina catalyst increased the olefin content in the product, which is consistent with our data.

The only prior art of which the applicants are aware relating to r for improving the stability of a cobalt F-T catalyst was reported by Eidus and Bulanova U.S.S.R. 150,102, Sept. 26, 1962, Appl. Nov. 27, 1954. In this work Zr was used in place of thorium to reduce the sensitivity of the catalyst to super heating.

SUMMARY OF THE INVENTION

The present invention is directed to a cobalt Fischer-Tropsch Catalyst/Molecular Sieve combination which incorporates a newly developed molecular sieve which demonstrates improved performance as a catalyst support over previously known molecular sieve supports.

It has been found that the resultant catalyst demonstrates superior product selectivity and high stability which is evidenced by lower methane production, higher C5+ yields, increased olefin production, and longer catalyst life.

DESCRIPTION OF THE INVENTION

We have found a new zeolitic molecular sieve based support which greatly reduces the undesirable methane production of a cobalt Fischer-Tropsch catalyst combined with it. This decrease in methane production results from shifting of the product slate toward heavier more desirable product. A significant increase in product produced above the motor fuels range is observed, however, this is not considered a draw back since these heavier products could easily be hydroprocessed back into the motor fuel boiling point range. The molecular sieve support acts to reduce the hydrogenation ability of the cobalt catalyst, promoting hydrocarbon chain growth over chain termination. Consistent with this theory the olefin content of the F T product was increased, improving the value of the product, especially in the C5-range.

The molecular sieve support pertaining to this invention, denoted TC-123 consists of a steam treated, acid extracted form of the molecular sieve known as LZ-210 disclosed in U.S. Pat. Nos. 4,503,023 and 4,610,856. The best way known to practice this invention is to start with an LZ-210 with $SiO_2/Al_2O_3$ ratio of 8.0 or above. The preferred procedure for producing the LZ-210 material used in the present invention is disclosed by Stanillis in commonly assigned co-pending application Ser. No. 72,785, filed concurrently herewith. This procedure involves subjecting a Y-zeolite to an LZ-210 secondary synthesis procedure without a subsequent ammonium exchange step. This material may then be ammonium exchanged and is steamed at 750° C. for 1 hr in 100% steam followed by acid extraction in 3M HCL solution for 3 hrs under reflux conditions. The resultant material has the following properties: $SiO_2/Al_2O_3=200$, surface area (1 pt BETO=800 m2/g, and a x-ray A zero=24,260.

The support is subsequently pore filled with a solution such as ethylene glycol, water or alcohol containing $Co(NO_3)_2$ and a $Mn(NO_3)_4$ promoter to give a theoretical percentage of Co=8.2% and Mn=1.6%. The method of silica binding and shaping is not thought to be particularly important, in the context of the improvement taught in the present invention.

Characterization of the catalyst shows the promoted cobalt oxide encapsulated within the secondary pore structure of the TC-123 molecular sieve which was generated by the steam and acid extraction treatments. The secondary pores aid in tailoring and maintaining the cobalt particles at the optimum size for maximum activity and selectivity while allowing the syngas and products to diffuse through the primary zeolite pore structure.

The use of the novel catalyst system comprising cobalt and a steam treated acid extracted LZ-210 support as a Fischer-Tropsch catalyst is also taught.

The catalyst system of the present invention can most effectively be employed when promoted with a suitable Fischer-Tropsch catalyst promoter such as for example, Mn oxide, Zr Oxide and combinations thereof.

EXAMPLES

While the invention has been described above, the details of the present invention will be better understood by recourse of the following examples which serve to illustrate that for a Mn promoted cobalt F-T catalyst the use of a steam treated acid extracted LZ-210 molecular sieve support yields enhanced results when compared to the same catalyst over a known acid extracted UHP-Y molecular sieve (U.S. Pat. Nos. 4,401,556 Bezman et al., and 4,652,538 Rabo et al).

The following examples compare a manganese promoted acid extracted UHP-Y supported F T catalyst with the same catalyst using a steam treated, acid extracted LZ-210 molecular sieve support.

The catalysts were both prepared by the same procedure and run under identical conditions.

EXAMPLE I

The catalyst was prepared by pore filling 100.0 g anhydrous TC-123 with a warm ethylene glycol solution of 7.21 g Mn(NO$_3$)$_2$ xH$_2$O, 55.8 g Co(NO$_3$)$_2$ 6H$_2$O, and 48.0 g ethylene glycol. The catalyst was dried and calcined in air by the following procedure: 100°C. for 10 hrs, ramp to 200C in 0.5hr, soak at 200C for 0.5hr, ramp to 450C in 1.25 hrs, soak at 450C for 4 hrs. The resultant powder was silica bonded and extruded into ⅛" extrudates, dried at 110C overnight followed calcination at 250C for 2 hrs. The calculated percent components in the catalyst based on raw materials used were: Co=8.2, Mn=1.6, silica binder=15%, and TC-123=72.1.

A 80 cc sample was loaded into a Berty reactor where it was treated with H$_2$ at 300 psig at 350C for 18 hrs and exposed to 1:1 H$_2$: CO syngas at 220C. The catalyst was tested at 240C and 260C under various pressures and H2:CO ratios. The results of the tests are contained in Table 1.

EXAMPLE II

A second catalyst was prepared using the same method as that described in Example I, substituting acid extracted UHP Y molecular sieve for the TC-123 molecular sieve of Example I. The catalyst sample was tested in the same manner as in Example I, with the results shown in Table 1.

TABLE 1

Comparison of Co/Mn F-T Catalysts

| Catalyst Support | I<br>TC-123 | II<br>Acid Extracted<br>UHP-Y |
|---|---|---|
| Conversion (H2 + CO) | 47.8 | 42.8 |
| CH4 | 3.3 | 5.3 |
| C2–C4 | 7.8 | 9.7 |
| C5–350 F. | 21.4 | 23.0 |
| 350–650 F. | 29.0 | 31.5 |
| 650 F.+ | 38.6 | 30.4 |
| C5+ | 88.9 | 85.0 |
| C4 olefin/parifin | 3.7 | 2.1 |

Conditions: 240 C., 1:1 H2:CO, 300 psig, 300 GHSV

The TC-123 supported catalyst demonstrated a substantial reduction in methane and C2-4 production compared to the UHP Y supported catalyst while demonstrating comparable or higher syngas conversion. The reduced C1-4 fraction was realized in the more valuable C5+ fraction. The olefin content of the product was also found to be higher than the UHP-Y case as indicated by the olefin to paraffin ratio of the C4 fraction.

While the invention has been described with respect to various specific examples and embodiments, it is to be understood that the invention is not limited thereto and that it can be variously practiced within the scope of the following claims.

We claim

1. A cobalt Fischer-Tropsch catalyst supported by a steam treated, acid extracted LZ-210 molecular sieve.

2. A catalyst according to claim 1 wherein the acid extracted LZ-210 has a SiO$_2$/Al$_2$O$_3$ ratio of 8.0 or above.

3. A catalyst according to claim 1 wherein the LZ-210 is steam treated at 750° C. for 1 hour in 100% steam followed by acid extraction.

* * * * *